United States Patent
Deng

(10) Patent No.: US 10,407,404 B2
(45) Date of Patent: Sep. 10, 2019

(54) PHYSICAL FORM OF A SGR MODULATOR

(71) Applicant: ASTRAZENECA AB, Sodertalje (SE)

(72) Inventor: Chaoyi Deng, Shanghai (CN)

(73) Assignee: ASTRAZENECA AB, Sodertalje (SE)

( * ) Notice: Subject to any disclaimer, the term of this patent is extended or adjusted under 35 U.S.C. 154(b) by 0 days.

(21) Appl. No.: 16/085,717

(22) PCT Filed: Mar. 22, 2017

(86) PCT No.: PCT/EP2017/056838
§ 371 (c)(1),
(2) Date: Sep. 17, 2018

(87) PCT Pub. No.: WO2017/162747
PCT Pub. Date: Sep. 28, 2017

(65) Prior Publication Data
US 2019/0106402 A1     Apr. 11, 2019

(30) Foreign Application Priority Data

Mar. 23, 2016    (WO) ................ PCT/CN2016/077095

(51) Int. Cl.
| C07D 401/14 | (2006.01) |
| C07D 401/14 | (2006.01) |
| A61P 11/06  | (2006.01) |
| A61P 19/02  | (2006.01) |
| C07D 401/04 | (2006.01) |
| C07D 403/12 | (2006.01) |

(52) U.S. Cl.
CPC ............ C07D 401/04 (2013.01); A61P 11/06 (2018.01); A61P 19/02 (2018.01); C07D 403/12 (2013.01); *C07B 2200/13* (2013.01)

(58) Field of Classification Search
CPC ........ C07D 401/14; A61P 11/06; A61P 19/02; C07B 2200/13
See application file for complete search history.

(56) References Cited

U.S. PATENT DOCUMENTS

2017/0298041 A1* 10/2017 Ripa .................... C07D 401/04

FOREIGN PATENT DOCUMENTS

| WO | WO 2008/076048 A1 | 6/2008 |
| WO | WO 2009/142569 A1 | 11/2009 |
| WO | WO 2013/001294 A1 | 1/2013 |
| WO | WO 2016/046260 A1 | 3/2016 |

OTHER PUBLICATIONS

International Search Report and Written Opinion for corresponding PCT/EP2017/056838 dated May 4, 2017.

* cited by examiner

*Primary Examiner* — Timothy R Rozof

(57) ABSTRACT

A crystalline form of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide (form C), pharmaceutical compositions containing it and its use in therapy.

11 Claims, 2 Drawing Sheets

Figure 1. XRPD diffractogram of Example 1 - Form C

PHYSICAL FORM OF A SGR MODULATOR

CROSS-REFERENCE TO RELATED APPLICATIONS

This application is a U.S. National Stage application of International Application No. PCT/EP2017/056838, filed on Mar. 22, 2017, said International Application No. PCT/EP2017/056838 claims benefit of International Application No. PCT/CN2016/077095, filed Mar. 23, 2016. Each of the above listed applications is incorporated by reference herein in its entirety for all purposes.

The present invention relates to a new physical form of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide, to pharmaceutical compositions containing it and its use in therapy.

Glucocorticoids (GCs) have been used for decades to treat acute and chronic inflammatory and immune conditions, including rheumatoid arthritis, asthma, chronic obstructive pulmonary disease ("COPD"), osteoarthritis, rheumatic fever, allergic rhinitis, systemic lupus erythematosus, Crohn's disease, inflammatory bowel disease, and ulcerative colitis. Examples of GCs include dexamethasone, prednisone, and prednisolone. Unfortunately, GCs are often associated with severe and sometimes irreversible side effects, such as osteoporosis, hyperglycemia, effects on glucose metabolism (diabetes mellitus), skin thinning, hypertension, glaucoma, muscle atrophy, Cushing's syndrome, fluid homeostasis, and psychosis (depression). These side effects can particularly limit the use of GCs in a chronic setting. Thus, a need continues to exist for alternative therapies that possess the beneficial effects of GCs, but with a reduced likelihood of side effects.

GCs complex with the GC receptor (GR) to regulate gene transcription. The GC-GR complex translocates to the cell nucleus, and then binds to GC response elements (GREs) in the promoter regions of various genes. The resulting GC-GR-GRE complex, in turn, activates or inhibits transcription of proximally located genes. The GC-GR complex also (or alternatively) may negatively regulate gene transcription by a process that does not involve DNA binding. In this process, termed transrepression, the GC-GR complex enters the nucleus and directly interacts (via protein-protein interaction) with other transcription factors, repressing their ability to induce gene transcription and thus protein expression.

Some of the side effects of GCs are believed to be the result of cross-reactivity with other steroid receptors (e.g., progesterone, androgen, mineralocorticoid, and estrogen receptors), which have somewhat homologous ligand binding domains; and/or the inability to selectively modulate gene expression and downstream signaling. Consequently, it is believed that an efficacious selective GR modulator (SGRM), which binds to GR with greater affinity relative to other steroid hormone receptors, would provide an alternative therapy to address the unmet need for a therapy that possesses the beneficial effects of GCs, while, at the same time, having fewer side effects.

A range of compounds have been reported to have SGRM activity. See, e.g., WO2007/0467747, WO2007/114763, WO2008/006627, WO2008/055709, WO2008/055710, WO2008/052808, WO2008/063116, WO2008/076048, WO2008/079073, WO2008/098798, WO2009/065503, WO2009/142569, WO2009/142571, WO2010/009814, WO2013/001294, and EP2072509. Still, there continues to be a need for new SGRMs that exhibit, for example, an improved potency, efficacy, effectiveness in steroid-insensitive patients, selectivity, solubility allowing for oral administration, pharmacokinetic profile allowing for a desirable dosing regimen, stability on the shelf (e.g., hydrolytic, thermal, chemical, or photochemical stability), crystallinity, tolerability for a range of patients, side effect profile and/or safety profile.

In the formulation of drug substances, it is important for the drug substance (active compound) to be in a form in which it can be conveniently handled and processed. This is of importance, not only from the point of view of obtaining a commercially-viable manufacturing process for the drug substance itself, but also from the point of view of subsequent manufacture of pharmaceutical formulations comprising the active compound and suitable excipients. In this connection, the chemical stability and the physical stability of the active compound are important factors. The active compound, and formulations containing it, should be capable of being effectively stored over appreciable periods of time, without exhibiting any significant change in the physico-chemical characteristics (e.g. chemical composition, density, hygroscopicity and solubility) of the active compound.

The structure of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide (hereafter "Compound (I)") is shown below:

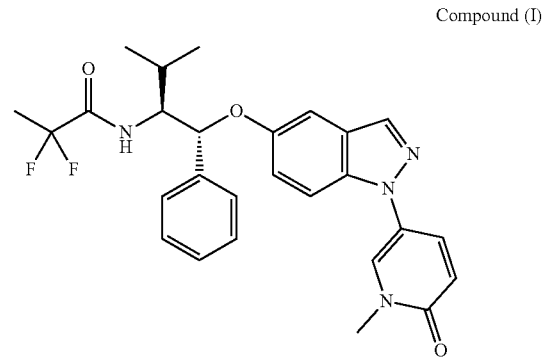 [SMILES: CC(C)[C@H](NC(=O)C(C)(F)F)[C@H](Oc1ccc2c(cnn2-c2ccc(=O)n(C)c2)c1)c1ccccc1]

Compound (I)

We have found that Compound I may exist in a number of crystalline forms. One crystalline form of Compound I "Form C" provides an X-ray powder diffraction pattern substantially as shown in FIG. 1.

One aspect of the invention provides a physical form of Compound (I) which exhibits the characteristic X-ray powder diffraction peaks (expressed in degrees 2θ) as shown in the appropriate Table 1 below.

Unless stated otherwise, all of the X-ray powder diffraction data described herein was obtained using CuKα radiation as described in the Examples.

In an embodiment of the invention, the compound has crystalline properties and in one aspect is at least 50% crystalline, in another aspect is at least 60% crystalline, in another aspect is at least 70% crystalline, in another aspect is at least 80% crystalline and in another aspect is 90% crystalline. Crystallinity may be estimated by conventional X-ray diffractometry techniques.

In another embodiment of the invention, the Compound (I) is from 50%, 60%, 70%, 80% or 90% to 95%, 96%, 97%, 98%, 99% or 100% crystalline.

The most prominent peaks of Compound (I) Form C are shown in Table 1.

According to a further aspect of the invention there is provided Compound (I) Form C, characterised in that said Form C has an X-ray powder diffraction pattern with at least one specific peak at 2θ about =7.3, 8.7, 12.5, 19.0 and/or 22.9°.

According to a further aspect of the invention there is provided Compound (I) Form C, characterised in that said Form C has an X-ray powder diffraction pattern with at least 2 specific peaks at 2θ about =7.3, 8.7, 12.5, 19.0 and/or 22.9°.

According to a further aspect of the invention there is provided Compound (I) Form C, characterised in that said Form C has an X-ray powder diffraction pattern with at least 3 specific peaks at 2θ about =7.3, 8.7, 12.5, 19.0 and/or 22.9°.

According to a further aspect of the invention there is provided Compound (I) Form C, characterised in that said Form C has an X-ray powder diffraction pattern with at least one specific peak at 2θ about =7.3, 8.7, 11.4, 12.5, 15.3, 17.3, 17.6, 19.0, 22.9 and/or 25.7°. According to a further aspect of the invention there is provided Compound (I) Form C, characterised in that said Form C has an X-ray powder diffraction pattern with at least one specific peak at 2θ about =7.3, 8.7, 11.4, 12.5, 15.3, 17.6 and/or 25.7°.

According to a further aspect of the invention there is provided Compound (I) Form C, characterised in that said Form C has an X-ray powder diffraction pattern with at least one specific peak at 2θ about =7.3, 8.7, 11.4, 12.5, 15.3, 17.6 and/or 25.6°.

According to a further aspect of the invention there is provided Compound (I) Form C, characterised in that said Form C has an X-ray powder diffraction pattern with at least 2 specific peaks at 2θ about =7.3, 8.7, 11.4, 12.5, 15.3, 17.3, 17.6, 19.0, 22.9 and/or 25.7°.

According to a further aspect of the invention there is provided Compound (I) Form C, characterised in that said Form C has an X-ray powder diffraction pattern with at least 2 specific peaks at 2θ about =7.3, 8.7, 11.4, 12.5, 15.3, 17.3, 17.6, 19.0, 22.9 and/or 25.6°.

According to a further aspect of the invention there is provided Compound (I) Form C, characterised in that said Form C has an X-ray powder diffraction pattern with at least 2 specific peaks at 2θ about =7.3, 8.7, 11.4, 12.5, 15.3, 17.6 and/or 25.7°.

According to a further aspect of the invention there is provided Compound (I) Form C, characterised in that said Form C has an X-ray powder diffraction pattern with at least 2 specific peaks at 2θ about =7.3, 8.7, 11.4, 12.5, 15.3, 17.6 and/or 25.6°.

According to a further aspect of the invention there is provided Compound (I) Form C, characterised in that said Form C has an X-ray powder diffraction pattern with at least 3 specific peaks at 2θ about =7.3, 8.7, 11.4, 12.5, 15.3, 17.3, 17.6, 19.0, 22.9 and/or 25.7°.

According to a further aspect of the invention there is provided Compound (I) Form C, characterised in that said Form C has an X-ray powder diffraction pattern with at least 3 specific peaks at 2θ about =7.3, 8.7, 11.4, 12.5, 15.3, 17.3, 17.6, 19.0, 22.9 and/or 25.6°.

According to a further aspect of the invention there is provided Compound (I) Form C, characterised in that said Form C has an X-ray powder diffraction pattern with specific peaks at 2θ about =7.3, 8.7, 12.5, 19.4 and 23.6°.

According to a further aspect of the invention there is provided Compound (I) Form C, characterised in that it has an X-ray powder diffraction pattern with specific peaks at 2θ about =7.3, 8.7, 12.5, 15.3 and 23.6°

According to a further aspect of the invention there is provided Compound (I) Form C, characterised in that it has an X-ray powder diffraction pattern with at least one specific peak is at 2θ about =7.3, 8.7, 12.5 and/or 15.3°

According to a further aspect of the invention there is provided Compound (I) Form C, characterised in that said Form C has an X-ray powder diffraction pattern with at least 2 specific peaks at 2θ about =7.3, 8.7, 12.5 and/or 15.3°.

According to a further aspect of the invention there is provided Compound (I) Form C, characterised in that said Form C has an X-ray powder diffraction pattern with at least 2 specific peaks at 2θ about =7.3, 8.7, 12.5, 15.3 and/or 19.0°.

According to a further aspect of the invention there is provided Compound (I) Form C, characterised in that said Form C has an X-ray powder diffraction pattern with at least 3 specific peaks at 2θ about =7.3, 8.7, 12.5, 15.3 and/or 19.0°.

According to a further aspect of the invention there is provided Compound (I) Form C, characterised in that said Form C has an X-ray powder diffraction pattern with specific peaks at 2θ about =7.3, 8.7, 12.4, 12.5, 19.4 and 23.6°.

According to a further aspect of the invention there is provided Compound (I) Form C, characterised in that said Form C has an X-ray powder diffraction pattern with specific peaks at 2θ about =7.3, 8.7, 11.4, 12.5, 14.5, 15.3, 17.6, 19.4, 23.6 and 25.7°.

According to a further aspect of the invention there is provided Compound (I) Form C, characterised in that said Form C has an X-ray powder diffraction pattern with at least one specific peak at 2θ=7.3, 8.7, 12.5, 19.0 and/or 22.9°.

According to a further aspect of the invention there is provided Compound (I) Form C, characterised in that said Form C has an X-ray powder diffraction pattern with at least 2 specific peaks at 2θ=7.3, 8.7, 12.5, 19.0 and/or 22.9°.

According to a further aspect of the invention there is provided Compound (I) Form C, characterised in that said Form C has an X-ray powder diffraction pattern with at least 3 specific peaks at 2θ=7.3, 8.7, 12.5, 19.0 and/or 22.9°.

According to a further aspect of the invention there is provided Compound (I) Form C, characterised in that said Form C has an X-ray powder diffraction pattern with at least one specific peak at 2θ=7.3, 8.7, 11.4, 12.5, 15.3, 17.3, 17.6, 19.0, 22.9 and 25.7°.

According to a further aspect of the invention there is provided Compound (I) Form C, characterised in that said Form C has an X-ray powder diffraction pattern with at least 2 specific peaks at 2θ=7.3, 8.7, 11.4, 12.5, 15.3, 17.3, 17.6, 19.0, 22.9 and/or 25.7°.

According to a further aspect of the invention there is provided Compound (I) Form C, characterised in that said Form C has an X-ray powder diffraction pattern with at least 3 specific peaks at 2θ=7.3, 8.7, 11.4, 12.5, 15.3, 17.3, 17.6, 19.0, 22.9 and/or 25.7°.

According to a further aspect of the invention there is provided Compound (I) Form C, characterised in that said Form C has an X-ray powder diffraction pattern with specific peaks at 2θ=7.3, 8.7, 12.5 and 23.6°.

According to a further aspect of the invention there is provided Compound (I) Form C, characterised in that said Form C has an X-ray powder diffraction pattern with specific peaks at 2θ=7.3, 8.7, 12.5, 19.4 and 23.6°.

According to a further aspect of the invention there is provided Compound (I) Form C, characterised in that said Form C has an X-ray powder diffraction pattern with specific peaks at 2θ=7.3, 8.7, 12.5, 15.3 and 23.6°.

According to a further aspect of the invention there is provided Compound (I) Form C, characterised in that said Form C has an X-ray powder diffraction pattern with specific peaks at 2θ=7.3, 8.7, 11.4, 12.5, 15.3, 17.6 and 23.6°.

According to a further aspect of the invention there is provided Compound (I) Form C, characterised in that said Form C has an X-ray powder diffraction pattern with specific peaks at 2θ=7.3, 8.7, 11.4, 12.5, 14.5, 15.3, 17.6, 19.4, 23.6 and 25.6°.

According to a further aspect of the invention there is provided Compound (I) Form C, characterised in that said Form C has an X-ray powder diffraction pattern with specific peaks at 2θ=7.3, 8.7, 11.4, 12.5, 14.5, 15.3, 17.6, 19.4, 23.6 and 25.7°.

According to a further aspect of the invention there is provided Compound (I) Form C, characterised in that said Form C has an X-ray powder diffraction pattern substantially as shown in FIG. 1.

When heated in a Differential Scanning Calorimeter (DSC) (conditions as described in the Examples section) the Compound (I) Form C exhibits a melting with an onset temperature at about 160.6° C., and a peak temperature at about 162.6° C. as illustrated in FIG. 2.

A person skilled in the art understands that the value or range of values observed in a particular compound's DSC Thermogram will show variation between batches of different purities. Therefore, whilst for one compound the range may be small, for others the range may be quite large. Generally, a measurement error of a diffraction angle in DSC thermal events is approximately plus or minus 5° C., and such degree of a measurement error should be taken into account when considering the DSC data included herein.

Therefore, in one embodiment there is provided a crystalline form, Compound (I) form C, which has a DSC endotherm with an onset of melting at about 160.6° C. and a peak at about 162.6° C.

Therefore, in one embodiment there is provided a crystalline form, Compound (I) form C, which has a DSC endotherm with an onset of melting at 160.6° C. plus or minus 5° C. and a peak at 162.6° C. plus or minus 5° C.

In one embodiment there is provided a crystalline form, Compound (I) form C, which has a DSC endotherm with an onset of melting at 160.6° C. and a peak at 162.6° C.

In one embodiment there is provided a crystalline form, Compound (I) form C, which has a DSC thermogram substantially as shown in FIG. 2.

Crystallisation of the Form C in the process described herein may be aided by seeding with crystals of the Form C. The seed crystals may be obtained using one of the methods described in the Examples. The use of seeding is particularly advantageous in larger-scale manufacture.

Where herein the compound described as having "X-ray powder diffraction pattern with at least one specific peak at 2θ about = . . . " the XRPD of the compound may contain one or more of the 2θ values listed. For example one or more of the 2θ values, 2 or more of the 2θ values or 3 or more of the 2θ values listed.

In the preceding paragraphs defining the X-ray powder diffraction peaks for the crystalline form of Compound (I), the term "about ="is used in the expression" . . . at 2θ about = . . . " to indicate that the precise position of peaks (i.e. the recited 2-theta angle values) should not be construed as being absolute values because, as will be appreciated by those skilled in the art, the precise position of the peaks may vary slightly between one measurement apparatus and another, from one sample to another, or as a result of slight variations in measurement conditions utilised. It is also stated in the preceding paragraphs that the crystalline form of Compound (I) provide X-ray powder diffraction patterns 'substantially' the same as the X-ray powder diffraction patterns shown in FIG. 1 has substantially the most prominent peaks (2-theta angle values) shown in Table 1. It is to be understood that the use of the term 'substantially' in this context is also intended to indicate that the 2-theta angle values of the X-ray powder diffraction patterns may vary slightly from one apparatus to another, from one sample to another, or as a result of slight variations in measurement conditions utilised, so the peak positions shown in the Figure or quoted in the Table are again not to be construed as absolute values.

The person skilled in the art of X-ray powder diffraction will realize that the relative intensity of peaks can be affected by, for example, grains above approximately 30 micrometer in size and non-unitary aspect ratios which may affect analysis of samples. Furthermore, it should be understood that intensities may fluctuate depending on experimental conditions and sample preparation such as preferred orientation of the particles in the sample. The use of automatic or fixed divergence slits will also influence the relative intensity calculations. A person skilled in the art can handle such effects when comparing diffraction patterns.

The person skilled in the art of X-ray powder diffraction will also realize that due to difference in sample heights and errors in the calibration of the detector position, a small shift in the 2θ positions could occur. Generally, a difference of ±0.1 from the given value are to be considered correct.

The Compound (I) form C described herein may also be characterised and/or distinguished from other physical forms using other suitable analytical techniques, for example NIR spectroscopy or solid-state nuclear magnetic resonance spectroscopy.

The chemical structure of Compound (I) form C described herein can be confirmed by routine methods for example proton nuclear magnetic resonance (NMR) analysis.

Compound (I) form C may be prepared as described in the Example hereinafter.

Diseases and Medical Conditions

Compound (I) form C may be useful as an anti-inflammatory agent, and may also display antiallergic, immunosuppressive and anti-proliferative actions. Thus, it is contemplated that compound (I) form C may be used as a medicament for the treatment or prophylaxis of one or more of the following conditions (generally a disorder) in a mammal:

(i) lung diseases, which coincide with inflammatory, allergic and/or proliferative processes, including chronically obstructive lung diseases of any origin (including bronchial asthma, chronic obstructive pulmonary disease (COPD)), bronchitis of different origins, adult respiratory forms of restructive lung diseases (including allergic alveolitis), all forms of pulmonary edema (including toxic pulmonary edema), sarcoidoses, and granulomatoses (including Boeck's disease);

(ii) allergies, which coincide with inflammatory, allergic and/or proliferative processes, including all forms of allergic reactions (including Quincke's edema; insect bites; allergic reactions to pharmaceutical agents, blood derivatives, contrast media, etc.; anaphylactic shock; urticaria; and allergic vascular diseases), allergic vasculitis, and inflammatory vasculitis;

(iii) rheumatic diseases/auto-immune diseases/degenerative joint diseases, which coincide with inflammatory, allergic and/or proliferative processes, including all forms of rheumatic diseases including rheumatoid arthritis, acute rheumatic fever, polymyalgia rheumatica, Behget's disease, reactive arthritis, spondyloarthritides including ankylosing spondylitis and psoriatric arthritis, systemic lupus erythematodes, discoid lupus erythematosus, sclerodermia, polymyositis, dermatomyositis, polyarteritis nodosa, Sjögren's syndrome, IgG4-associated disease, Still syndrome, Felty's syndrome, gout, vitiligo, and inflammatory soft-tissue diseases of other origins, and arthritic symptoms in degenerative joint diseases (osteoarthritis); and traumatic arthritides;

(iv) vascular inflammations (vasculitides), including erythema nodosum, polyarteris nodosa, granulomatosis with polyangitis, microscopic polyangitis, eosinophilic granulomatosis with polyangitis, Takayasu arteritis, Kawasaki disease, giant-cell arteritis (temporal arteritis), Henoch-Schonleins purpura and cryoglobulinemic vasculitis.

(v) nephropathies, which coincide with inflammatory, allergic and/or proliferative processes, including nephrotic syndrome and all nephritides (including glomerulonephritis); (vi) liver diseases, which coincide with inflammatory, allergic and/or proliferative processes, including acute liver cell decomposition, acute hepatitis of different origins (including virally-, toxically- or pharmaceutical agent-induced), and chronically aggressive and/or chronically intermittent hepatitis;

(vii) gastrointestinal diseases, which coincide with inflammatory, allergic and/or proliferative processes, including regional enteritis (Crohn's disease), gastritis, reflux esophagitis, ulcerative colitis, and gastroenteritis of other origins (including native sprue);

(viii) proctological diseases, which coincide with inflammatory, allergic and/or proliferative processes, including anal eczema, fissures, haemorrhoids, and idiopathic proctitis; (ix) eye diseases, which coincide with inflammatory, allergic and/or proliferative processes, including allergic keratitis, uvenitis iritis, conjunctivitis, blepharitis, optic neuritis, chorioiditis, and sympathetic ophthalmia;

(x) diseases of the ear-nose-throat area, which coincide with inflammatory, allergic and/or proliferative processes, including allergic rhinitis, hay fever, otitis externa (caused by contact dermatitis, infection, etc.), and otitis media;

(xi) neurological diseases, which coincide with inflammatory, allergic and/or proliferative processes, including primary cerebral vasculitis, cerebral edema (including tumor-induced cerebral edema), multiple sclerosis, acute encephalomyelitis, different forms of convulsions (including infantile nodding spasms), meningitis, spinal cord injury, and stroke;

(xii) blood diseases, which coincide with inflammatory, allergic and/or proliferative processes, including acquired haemolytic anemia, thrombocytopenia (including idiopathic thrombocytopenia), M. Hodgkins and Non-Hodgkins lymphomas, thrombocythemias, and erythrocytoses;

(xiii) tumor diseases, which coincide with inflammatory, allergic and/or proliferative processes, including acute lymphatic leukaemia, malignant lymphoma, lymphogranulomatoses, lymphosarcoma, and extensive metastases (including breast and prostate cancers);

(xiv) endocrine diseases, which coincide with inflammatory, allergic and/or proliferative processes, including endocrine orbitopathy, thyrotoxic crisis, de Quervain's thyroiditis, Hashimoto's thyroiditis, hyperthyroidism, Basedow's disease, granulomatous thyroiditis, lymphadenoid goiter;

(xv) transplants, which coincide with inflammatory, allergic and/or proliferative processes;

(xvi) severe shock conditions, which coincide with inflammatory, allergic and/or proliferative processes, including anaphylactic shock;

(xvii) substitution therapy, which coincides with inflammatory, allergic and/or proliferative processes, including innate primary suprarenal insufficiency (including congenital adrenogenital syndrome), acquired primary suprarenal insufficiency (including Addison's disease, autoimmune adrenalitis, meta-infective, tumors, metastases, etc.), innate secondary suprarenal insufficiency (including example congenital hypopituitarism), and acquired secondary suprarenal insufficiency (including meta-infective, tumors, etc.);

(xviii) Emesis, which coincides with inflammatory, allergic and/or proliferative processes, including in combination with a $5\text{-HT}_3$-antagonist in cytostatic-agent-induced vomiting;

(xix) Pains of inflammatory origins, including lumbago; and (xx) Dermatological diseases, which coincide with inflammatory, allergic and/or proliferative processes, including atopic dermatitis (including in children), exfoliative dermatitis, psoriasis, erythematous diseases (triggered by different noxae, including radiation, chemicals, burns, etc.), acid burns, bullous dermatoses (including autoimmune pemphigus vulgaris, and bullous pemphigoid), diseases of the lichenoid group, itching (including allergic origins), all forms of eczema (including atopic eczema or seborrheal eczema), rosacea, pemphigus vulgaris, erythema exudativum multiforme, erythema nodosum, balanitis, pruritis (including of allergic origin), manifestation of vascular diseases, vulvitis, inflammatory hair loss (including alopecia areata), cutaneous T-cell lymphoma, rashes of any origin or dermatoses, psoriasis and parapsoriasis groups, and pityriasis rubra pilaris.

Without prejudice to the foregoing, it is contemplated the compounds disclosed in this specification may be used to treat conditions such as: diabetes type I (insulin-dependent diabetes), Guillain-Barré syndrome, restenoses after percutaneous transluminal angioplasty, Alzheimer's disease, acute and chronic pain, arteriosclerosis, reperfusion injury, thermal injury, multiple organ injury secondary to trauma, acute purulent meningitis, necrotizing enterocolitis and syndromes associated with hemodialysis, leukopheresis, granulocyte transfusion, Conies Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, oesophageal varicies, muscle weakness, increased melanin pigmentation of the skin, weight loss, hypotension, hypoglycemia, polyuria, polydipsia, inflammation, autoimmune disorders, tissue rejection associated with organ transplant, malignancies such as leukemias and lymphomas, rheumatic fever, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, hypercalcemia, acute adrenal insufficiency, chronic primary adrenal insufficiency, secondary adrenal insufficiency, congenital adrenal hyperplasia, Little's syndrome, systemic inflammation, inflammatory bowel disease, Wegener's granulomatosis, giant cell arthritis, osteoarthritis, angioneurotic edema, tendonitis, bursitis, autoimmune chronic active hepatitis, hepatitis, cirrhosis, panniculitis, inflamed cysts, pyoderma gangrenosum, eosinophilic fasciitis, relapsing polychondritis, sarcoidosis Sweet's disease, type 1 reactive leprosy, capillary hemangiomas, lichen planus, erythema nodosum acne, hirsutism, toxic epidermal necrolysis, erythema multiform, psychoses, cognitive disorders (such as memory disturbances) mood disorders (such as depression and bipolar disorder), anxiety disorders and personality disorders.

As used herein, the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As will be appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear.

Some embodiments in this specification are directed to Compound (I) form C for use in therapy.

Some embodiments in this specification are directed to Compound (I) form C for use in treating a GR-mediated condition (such as a condition described above).

Some embodiments in this specification are directed to Compound (I) form C for use in treating an inflammatory or immune condition responsive to a steroidal glucocorticoid (e.g., dexamethasone, prednisone, and/or prednisolone).

Some embodiments in this specification are directed to Compound (I) form C for use in treating an inflammatory condition.

Some embodiments in this specification are directed to Compound (I) form C for use in treating a respiratory condition.

Some embodiments in this specification are directed to Compound (I) form C for use in treating a rheumatic condition.

Some embodiments in this specification are directed to Compound (I) form C for use in treating rheumatoid arthritis.

Some embodiments in this specification are directed to Compound (I) form C for use in treating asthma.

Some embodiments in this specification are directed to Compound (I) form C for use in treating moderate to severe asthma exacerbation.

Some embodiments in this specification are directed to Compound (I) form C for use in treating COPD.

Some embodiments in this specification are directed to Compound (I) form C for use in treating moderate to severe COPD exacerbation.

Some embodiments in this specification are directed to Compound (I) form C for use in treating irritable bowel syndrome.

Some embodiments in this specification are directed to Compound (I) form C for use in treating a collagen disorder.

Some embodiments in this specification are directed to Compound (I) form C for use in the prophylaxis of kidney transplant rejection.

Some embodiments in this specification are directed to Compound (I) form C for use in treating sarcoidosis.

Some embodiments in this specification are directed to Compound (I) form C for use in treating Addison's disease.

Some embodiments in this specification are directed to Compound (I) form C for use in treating chronic lymphocytic leukemia.

Some embodiments in this specification are directed to Compound (I) form C for use in treating acute lymphocytic leukemia.

Some embodiments in this specification are directed to Compound (I) form C for use in treating respiratory distress syndrome.

Some embodiments in this specification are directed to Compound (I) form C for use in treating nephrotic syndrome.

Some embodiments in this specification are directed to Compound (I) form C for use in treating a dermatologic disease.

Some embodiments in this specification are directed to Compound (I) form C for use in the manufacture of a medicament for therapy.

Some embodiments in this specification are directed to Compound (I) form C for use in the manufacture of a medicament for treating a GR-mediated condition (such as a condition described above).

Some embodiments in this specification are directed to Compound (I) form C for use in the manufacture of a medicament for treating an inflammatory or immune condition responsive to a steroidal glucocorticoid (e.g., dexamethasone, prednisone, and/or prednisolone).

Some embodiments in this specification are directed to Compound (I) form C for use in the manufacture of a medicament for treating an inflammatory condition.

Some embodiments in this specification are directed to Compound (I) form C for use in the manufacture of a medicament for treating a respiratory condition.

Some embodiments in this specification are directed to Compound (I) form C for use in the manufacture of a medicament for treating a rheumatic condition.

Some embodiments in this specification are directed to Compound (I) form C for use in the manufacture of a medicament for treating rheumatoid arthritis.

Some embodiments in this specification are directed to Compound (I) form C for use in the manufacture of a medicament for treating asthma.

Some embodiments in this specification are directed to Compound (I) form C for use in the manufacture of a medicament for treating moderate to severe asthma exacerbation.

Some embodiments in this specification are directed to Compound (I) form C for use in the manufacture of a medicament for treating COPD.

Some embodiments in this specification are directed to Compound (I) form C for use in the manufacture of a medicament for treating moderate to severe COPD exacerbation.

Some embodiments in this specification are directed to Compound (I) form C for use in the manufacture of a medicament for treating irritable bowel syndrome.

Some embodiments in this specification are directed to Compound (I) form C for use in the manufacture of a medicament for treating a collagen disorder.

Some embodiments in this specification are directed to Compound (I) form C for use in the manufacture of a medicament for prophylaxis of kidney transplant rejection.

Some embodiments in this specification are directed to Compound (I) form C for use in the manufacture of a medicament for treating sarcoidosis.

Some embodiments in this specification are directed to Compound (I) form C for use in the manufacture of a medicament for treating Addison's disease.

Some embodiments in this specification are directed to Compound (I) form C for use in the manufacture of a medicament for chronic lymphocytic leukemia.

Some embodiments in this specification are directed to Compound (I) form C for use in the manufacture of a medicament for treating acute lymphocytic leukemia.

Some embodiments in this specification are directed to Compound (I) form C for use in the manufacture of a medicament for treating respiratory distress syndrome.

Some embodiments in this specification are directed to Compound (I) form C for use in the manufacture of a medicament for treating nephrotic syndrome.

Some embodiments in this specification are directed to Compound (I) form C for use in the manufacture of a medicament for treating a dermatologic disease.

Some embodiments in this specification are directed to a method of treating a disease in a mammal in need of such treatment. The method comprises administering to the mammal a therapeutically effective amount of Compound (I) form C.

Some embodiments in this specification are directed to a method of treating a GR-mediated condition (such as a condition described above) in a mammal in need of such treatment. The method comprises administering to the mammal a therapeutically effective amount of Compound (I) form C.

Some embodiments in this specification are directed to a method of treating an inflammatory or immune condition responsive to a steroidal glucocorticoid (e.g., dexamethasone, prednisone, and/or prednisolone) in a mammal in need of such treatment. The method comprises administering to the mammal a therapeutically effective amount of Compound (I) form C.

Some embodiments in this specification are directed to a method of treating an inflammatory condition in a mammal in need of such treatment. The method comprises administering to the mammal a therapeutically effective amount of Compound (I) form C.

Some embodiments in this specification are directed to a method of treating a respiratory condition in a mammal in need of such treatment. The method comprises administering to the mammal a therapeutically effective amount of Compound (I) form C.

Some embodiments in this specification are directed to a method of treating a rheumatic condition in a mammal in need of such treatment. The method comprises administering to the mammal a therapeutically effective amount of Compound (I) form C.

Some embodiments in this specification are directed to a method of treating rheumatoid arthritis in a mammal in need of such treatment. The method comprises administering to the mammal a therapeutically effective amount of Compound (I) form C.

Some embodiments in this specification are directed to a method of treating asthma in a mammal in need of such treatment. The method comprises administering to the mammal a therapeutically effective amount of Compound (I) form C.

Some embodiments in this specification are directed to a method of treating moderate to severe asthma exacerbation in a mammal in need of such treatment. The method comprises administering to the mammal a therapeutically effective amount of Compound (I) form C.

Some embodiments in this specification are directed to a method of treating COPD in a mammal in need of such treatment. The method comprises administering to the mammal a therapeutically effective amount of Compound (I) form C.

Some embodiments in this specification are directed to a method of treating moderate to severe COPD exacerbation in a mammal in need of such treatment. The method comprises administering to the mammal a therapeutically effective amount of Compound (I) form C.

Some embodiments in this specification are directed to a method of treating irritable bowel syndrome in a mammal in need of such treatment. The method comprises administering to the mammal a therapeutically effective amount of Compound (I) form C.

Some embodiments in this specification are directed to a method of treating a collagen disorder in a mammal in need of such treatment. The method comprises administering to the mammal a therapeutically effective amount of Compound (I) form C.

Some embodiments in this specification are directed to a method of prophylaxis of kidney transplant rejection in a mammal in need of such treatment. The method comprises administering to the mammal a therapeutically effective amount of Compound (I) form C.

Some embodiments in this specification are directed to a method of treating sarcoidosis in a mammal in need of such treatment. The method comprises administering to the mammal a therapeutically effective amount of Compound (I) form C.

Some embodiments in this specification are directed to a method of treating Addison's disease in a mammal in need of such treatment. The method comprises administering to the mammal a therapeutically effective amount of Compound (I) form C.

Some embodiments in this specification are directed to a method of treating chronic lymphocytic leukemia in a mammal in need of such treatment. The method comprises administering to the mammal a therapeutically effective amount of Compound (I) form C.

Some embodiments in this specification are directed to a method of treating acute lymphocytic leukemia in a mammal in need of such treatment. The method comprises administering to the mammal a therapeutically effective amount of Compound (I) form C.

Some embodiments in this specification are directed to a method of treating respiratory distress syndrome in a mammal in need of such treatment. The method comprises administering to the mammal a therapeutically effective amount of Compound (I) form C.

Some embodiments in this specification are directed to a method of treating nephrotic syndrome in a mammal in need of such treatment. The method comprises administering to the mammal a therapeutically effective amount of Compound (I) form C.

Some embodiments in this specification are directed to a method of treating a dermatologic disease in a mammal in need of such treatment. The method comprises administering to the mammal a therapeutically effective amount of Compound (I) form C.

In some embodiments, the methods of treatment described above comprise orally administering to the mammal a therapeutically effective amount of Compound (I) form C.

In some embodiments, the treated mammal in the above-described methods of treatment is a human.

In some embodiments, the treated mammal in the above-described methods of treatment is a mammal other than a human. Such mammals include, for example, companion animals (e.g., dogs, cats, and horses), livestock animals (e.g., cattle and swine); lab animals (e.g., mice and rats); and wild, zoo, and circus animals (e.g., bears, lions, tigers, apes, and monkeys).

Pharmaceutical Compositions

Some embodiments of this specification are directed to pharmaceutical compositions (or medicaments) comprising Compound (I) form C, as well as processes for making such pharmaceutical compositions. In general, the pharmaceutical composition comprises a therapeutically effective amount of the compound. Pharmaceutical compositions comprising a compound described in this specification can vary widely. Although it is contemplated that a compound described in this specification could be administered by itself (i.e., without any other active or inactive ingredient), the pharmaceutical composition normally will instead comprise one or more additional active ingredients and/or inert ingredients. The inert ingredients present in the pharmaceutical compositions of this specification are sometimes collectively referred to as "excipients." Conventional procedures for the selection and preparation of suitable pharmaceutical formulations are described in, for example, "Pharmaceuticals—The Science of Dosage Form Designs", M. E. Aulton, Churchill Livingstone, $2^{nd}$ Ed. 2002.

It is contemplated that compositions comprising Compound (I) form C may be formulated for a variety of suitable routes and means of administration, including oral, rectal, nasal, topical, buccal, sublingual, vaginal, inhalation, insufflation, or parenteral administration. In some embodiments, the compound is administered orally. In some embodiments, the compound is administered intravenously. In some embodiments, the compound is administered intramuscularly. In some embodiments, the compound is administered subcutaneously. And, in some embodiments, the compound is administered intraperitoneally, intrathoracially, epidurally, intrathecally, intracerebroventricularly, and injection into the joints. In some embodiments, the compound is administered topically.

It is contemplated that pharmaceutical compositions of this specification may, for example, be in the form of solids, aqueous or oily solutions, suspensions, emulsions, creams, ointments, mists, gels, nasal sprays, suppositories, finely divided powders, and aerosols or nebulisers for inhalation.

In some embodiments, the composition comprises a liquid dosage form that may be administered orally.

In some embodiments, the composition comprises a solid dosage form that may be administered orally.

Solid form compositions may include, for example, powders, tablets, dispersible granules, capsules, cachets, and suppositories. A solid carrier may comprise one or more substances. Such substances are generally inert. A carrier also may act as, for example, a diluent, flavoring agent, solubilizer, lubricant, preservative, stabilizer, suspending agent, binder, or disintegrating agent. It also may act as, for example, an encapsulating material. Examples of often suitable carriers include pharmaceutical grade mannitol, lactose, magnesium carbonate, magnesium stearate, talc, lactose, sugar (e.g., glucose and sucrose), pectin, dextrin, starch, tragacanth, cellulose, cellulose derivatives (e.g., methyl cellulose and sodium carboxymethyl cellulose), sodium saccharin, low-melting wax, and cocoa butter.

In powders, the carrier is typically a finely divided solid, which is in a mixture with the finely divided active component. In tablets, the active component is typically mixed with the carrier having the desirable binding properties in suitable proportions and compacted into the desired shape and size.

For preparing suppository compositions, a low-melting wax (e.g., a mixture of fatty acid glycerides and cocoa butter) is typically first melted, followed by dispersing the active ingredient therein by, for example, stirring. The molten homogeneous mixture is then poured into convenient-sized molds and allowed to cool and solidify. Examples of non-irritating excipients that may be present in suppository compositions include, for example, cocoa butter, glycerinated gelatin, hydrogenated vegetable oils, mixtures of polyethylene glycols of various molecular weights, and fatty acid esters of polyethylene glycol.

Liquid compositions may be prepared by, for example, dissolving or dispersing the compound of this specification in a carrier, such as, for example, water, water/propylene glycol solutions, saline aqueous dextrose, glycerol, or ethanol. In some embodiments, aqueous solutions for oral administration may be prepared by dissolving a compound of this specification in water with a solubilizer (e.g., a polyethylene glycol). Colorants, flavoring agents, stabilizers, and thickening agents, for example, also may be added. In some embodiments, aqueous suspensions for oral use may be made by dispersing the compound of this specification in a finely divided form in water, together with a viscous material, such as, for example, one or more natural synthetic gums, resins, methyl cellulose, sodium carboxymethyl cellulose, or other suspending agents. If desired, the liquid composition also may contain other non-toxic auxiliary inert ingredients, such as, for example, wetting or emulsifying agents, pH buffering agents and the like, for example, sodium acetate, sorbitan monolaurate, triethanolamine sodium acetate, sorbitan monolaurate, triethanolamine oleate, etc. Such compositions also may contain other ingredients, such as, for example, one or more pharmaceutical adjuvants.

In some embodiments, the concentration of the compound (I) form C in the pharmaceutical composition is from about 0.05% to about 99% (by weight). In some such embodiments, for example, the concentration is from about 0.05 to about 80%, from about 0.10 to about 70%, or from about 0.10% to about 50% (by weight).

When a compound of this specification is administered as a sole therapy for treating a disorder, a "therapeutically effective amount" is an amount sufficient to reduce or completely alleviate symptoms or other detrimental effects of the condition; cure the condition; reverse, completely stop, or slow the progress of the condition; reduce the risk of the condition getting worse; or delay or reduce the risk of onset of the condition.

In some embodiments of this specification, the pharmaceutical composition is suitable for oral administration in a unit dosage form of, for example, a tablet or capsule containing from about 0.1 mg and about 10 g of the compound (I) form C.

In some embodiments, the pharmaceutical composition comprises an amount of Compound (I) form C that is therapeutically effective to treat a GR-mediated condition (such as a condition described above) desired to be treated.

In some embodiments, the pharmaceutical composition comprises an amount of Compound (I) that is therapeutically effective to treat an inflammatory condition.

In some embodiments, the pharmaceutical composition comprises an amount of Compound (I) form C that is therapeutically effective to treat a rheumatic condition.

The optimum dosage and frequency of administration will depend on the particular condition being treated and its severity; the species of the patient; the age, sex, size and weight, diet, and general physical condition of the particular patient; brain/body weight ratio; other medication the patient may be taking; the route of administration; the formulation; and various other factors known to physicians (in the context of human patients), veterinarians (in the context of non-human patients), and others skilled in the art.

It is contemplated that, in some embodiments, the optimum amount of a compound of this specification is at least about 0.01 mg/kg body weight per day, from about 0.01 to about 100 mg/kg body weight per day, or from about 0.01 to about 10 mg/kg body weight per day (e.g., 0.5 mg/kg body weight per day) when administered systemically.

It is contemplated that the pharmaceutical compositions can be in one or more unit dosage forms. Accordingly, the composition may be divided into unit doses containing appropriate quantities of the active component. The unit dosage form can be, for example, a capsule, cachet, or tablet itself, or it can be the appropriate number of any of these in packaged forms. The unit dosage form alternatively can be a packaged preparation in which the package contains discrete quantities of the composition, such as, for example, packeted tablets, capsules, or powders in vials or ampoules. Unit dosage forms may be prepared by, for example, various methods well known in the art of pharmacy.

It is contemplated that a dosage can be given once daily or in divided doses, such as, for example, from 2 to 4 times per day.

Combinations

This specification also is directed to combination therapies or compositions wherein a compound (I) comprising a compound (I), is administered concurrently (possibly in the same composition) or sequentially with one or more other active agents for the treatment of any of the above-discussed conditions.

In some embodiments in which a combination therapy is used, the amount of the compound of this specification and the amount of the other pharmaceutically active agent(s) are, when combined, therapeutically effective to treat a targeted disorder in the animal patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; reduce the risk of the disorder getting worse; or delay or reduce the risk of onset of the disorder. Typically, such amounts may be determined by one skilled in the art by, for example, starting with the dosage range described in this patent for the compound of this specification and an approved or otherwise published dosage range(s) of the other pharmaceutically active compound(s).

When used in a combination therapy, it is contemplated that the compound of this specification and the other active ingredients may be administered in a single composition, completely separate compositions, or a combination thereof. It also is contemplated that the active ingredients may be administered concurrently, simultaneously, sequentially, or separately. The particular composition(s) and dosing frequency(ies) of the combination therapy will depend on a variety of factors, including the route of administration, the condition being treated, the species of the patient, any potential interactions between the active ingredients when combined into a single composition, any interactions between the active ingredients when they are administered to the animal patient, and various other factors known to physicians (in the context of human patients), veterinarians (in the context of non-human patients), and others skilled in the art.

Kits

This specification also is directed, in part, to a kit comprising the compound (I) form C. In some embodiments, the kit further comprises one or more additional components, such as, for example: (a) an apparatus for administering the compound (I) form C; (b) instructions for administering the compound (I) form C; (c) an excipient (e.g., a re-suspending agent); or (d) an additional active ingredient, which may be in the same and/or different dosage forms as the compound (I) form C.

EXAMPLES

Figure 1:
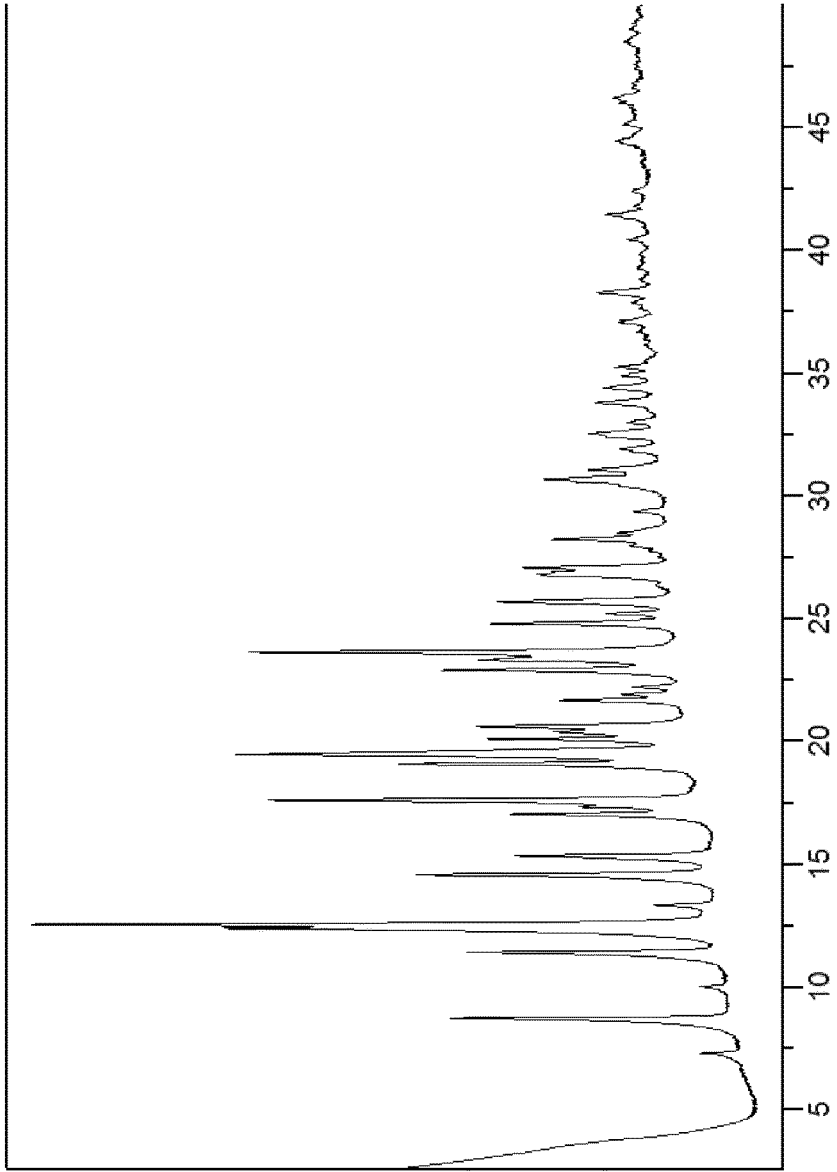
FIG. 1 shows an X-ray powder diffraction pattern of Example 1 (form C).
Figure 2:
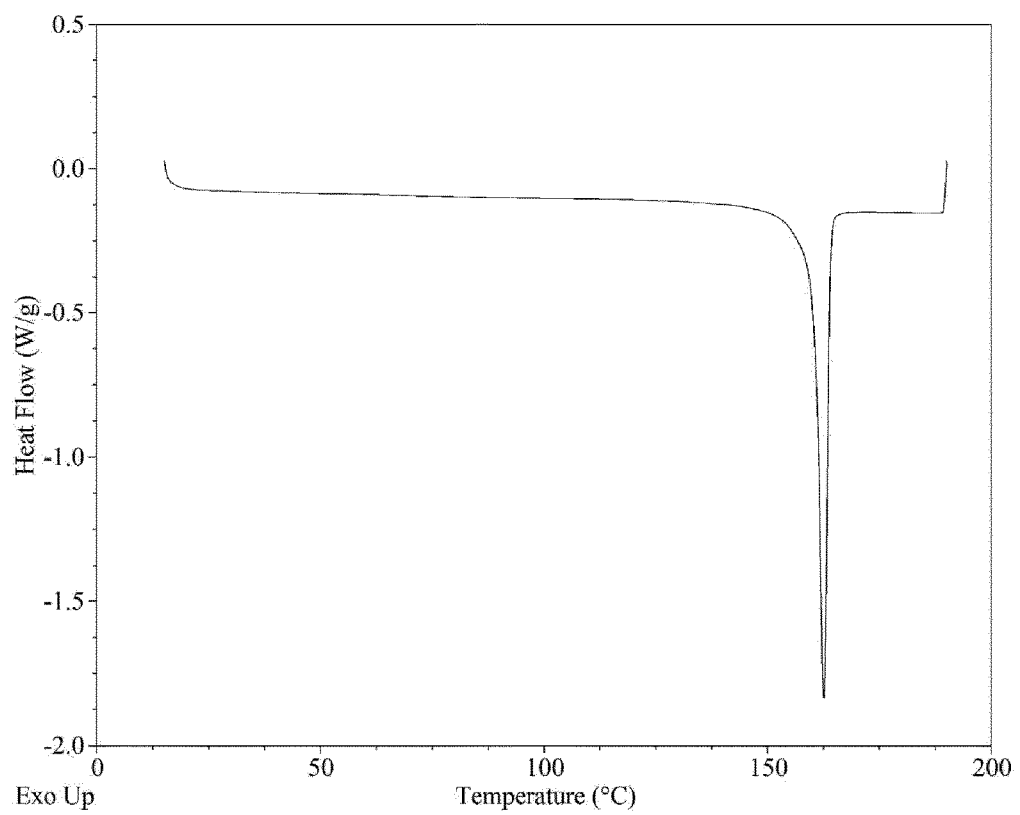
FIG. 2 shows DSC of Example 1 (form C).

The present invention will now be further explained by reference to the following illustrative examples in which, unless stated otherwise:

(i) Temperatures are given in degrees Celsius (° C.); operations were carried out at room or ambient temperature, that is, at a temperature in the range of 18-25° C.

(ii) In general, the course of reactions was followed by HPLC and reaction times are given for illustration only.

(iii) Yields are given for illustration only and are not necessarily those which can be obtained by diligent process development; preparations were repeated if more material was required.

(iv) Chemical symbols have their usual meanings; SI units and symbols are used.

(v) Solvent ratios are given in volume:volume (v/v) terms.

(vi) Unless stated otherwise, starting materials were commercially available.

Example

X-Ray Powder Diffraction Analysis

The X-ray diffraction analysis was performed according to standard methods, which can be found in e.g. Kitaigorodsky, A. I. (1973), Molecular Crystals and Molecules, Academic Press, New York; Bunn, C. W. (1948), Chemical Crystallography, Clarendon Press, London; or Klug, H. P. & Alexander, L. E. (1974), X-ray Diffraction Procedures, John Wiley & Sons, New York.

Samples were mounted on single silicon crystal (SSC) wafer mounts and powder X-ray diffraction was recorded with a PANalytical X'Pert PRO (reflection geometry, wavelength of X-rays 1.5418 Å nickel-filtered Cu radiation, Voltage 45 kV, filament emission 40 mA). Automatic variable divergence and anti scatter slits were used and the samples were rotated during measurement. Samples were scanned from 2-50° 2Theta using a 0.013° step width and 1415 seconds per step using a PIXCEL detector (active length 3.35° 2Theta).

It is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensities of peaks may vary according to the orientation of the sample under test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute and any crystalline form that provides a power diffraction pattern substantially identical to those disclosed herein fall within the scope of the present disclosure (for further information see Jenkins, R & Snyder, R. L. 'Introduction to X-Ray Powder Diffractometry' John Wiley & Sons, 1996).

Generally, a measurement error of a diffraction angle in an X-ray powder diffractogram may be approximately plus or minus 0.1° 2-theta, and such a degree of a measurement error should be taken into account when considering the X-ray powder diffraction data.

TABLE 1

Ten prominent peaks of Comopund (I) Form C when measured using CuKα radiation

| °2-theta |
| --- |
| 7.3 |
| 8.7 |
| 11.4 |
| 12.5 |
| 14.5 |
| 15.3 |
| 17.6 |
| 19.4 |
| 23.6 |
| 25.7 |

Additional peaks that may be useful to characterise Compound (I) form C are 17.3, 19.0 and 22.9° 2-theta. Yet further additional peaks that may be useful to characterise Compound (I) form C are 12.4 and 25.6° 2-theta.

General Methods

NMR spectra were recorded on a Bruker Avance, Avance II or Avance III spectrometer at a proton frequency of 300, 400, 500 or 600 MHz. The central peaks of chloroform-δ (H 7.26 ppm) or DMSO-$d_6$ (H 2.49 ppm) were used as internal references.

LC/MS experiments were performed using a Waters Acquity system combined with a Waters Xevo Q-ToF Mass or a Shimadzu 2010EV UPLC system in ESI mode. LC was run in two set ups: 1) BEH C18 column (1.7 μm 2.1×50 mm) in combination with a gradient (2-95% B in 5 min) of aqueous 46 mM ammonium carbonate/ammonia buffer at pH 10 (A) and MeCN (B) at a flow rate of 1.0 mL/min or in combination with a gradient (5-95% B in 2 min) of water and TFA (0.05%) (A) and $CH_3CN$ and TFA (0.05%) at a flow rate of 1.0 mL/min (B).

Optical purity, indicated as enantiomeric excess (% ee), was determined by:

Method A: chiral HPLC using an Agilent 1100 series chromatograph. System equipped with Chiralpak (IB-3, IA-3 or IC-3) 50×4.6 mm; 3 μm. As mobile phase hexane (0.1% triethylamine)/EtOH (85:15) with a flow rate of 1 mL/min was used. The injection volume was 3 μL and compound detection was performed by UV at 254 nm.

Method B: Chiral SFC system equipped with Chiralpak (IC or AD-H) 150×4.6 mm, 3 μm or Chiracel (OD-H, OJ-3, OD-3) or Lux 5u Cellulose-3. As eluent gradients of $CO_2$ (100 g/min, 120 bar, 40° C.) (A) and 5-40% MeOH/diethylamine (0.1%), EtOH/diethylamine (0.1%), 20% isopropylalcohol or 20% isopropylalcohol/$NH_3$ 200:1 (B) were applied with a flow rate of 4 mL/min. The injection volume was 0.7 μL or 10 μL and compound detection was performed by UV at 254 nm or 220 nm.

Preparative HPLC was performed with a Waters FractionLynx system with integrated MS detection and equipped with Prep C18 OBD 5 μm 19×150 mm columns from X-Bridge or Sunfire. Alternatively Gilson GX-281 with integrated UV detection was used, equipped with either Kromasil C8 10 μm, 20×250 ID or 50×250 ID mm. As eluent (acidic) gradients of water/MeCN/acetic acid (95/5/0.1) or water/0.05% TFA (A) and MeCN/0.05% TFA (B) or (basic) MeCN or MeOH (A) and 0.03% ammonia in water or 0.03% $NH_4HCO_3$ (B) were applied.

Unless otherwise stated, starting materials used in the below examples were commercially available or previously described in the literature. All solvents and commercial reagents were of laboratory grade, and were used as received unless otherwise stated.

All temperatures are in degrees Celsius (° C.). In general, unless otherwise stated, operations discussed in the below examples were carried out at room or ambient temperature (18-25° C.); reaction progress was monitored by HPLC, LC-MS or TLC; oven-dried standard laboratory glassware was used and routine manipulations were conducted at ambient temperature under a blanket of $N_2$; evaporations were performed under reduced pressure using a rotary evaporator or other standard distillation equipment; and products were dried under reduced pressure at a suitable temperature.

The names of the compounds exemplified in this patent were generated using ChemDraw Ultra 11.0. This is a chemical-name-generating program that assigns chemical names to drawn structures at the press of a button.

Differential Scanning Calorimetry (DSC)

Using standard methods (for example those described in Hohne, G. W. H. et al (1996), Differential Scanning Calorimetry, Springer, Berlin) the calorimetric response of a test sample to increasing temperature was investigated using a TA Instruments Q2000 Differential Scanning Calorimeter (DSC). Measurements were performed between 15° C. and 190° C. a ramp rate of 5° C. per minute. Approximately 0.5 to 5 mg of test sample was placed in aluminium pans with lids (no crimping) under a flow of nitrogen gas (50 mL/min).

As mentioned hereinbefore, it is well known that the DSC onset and peak temperatures may vary according to the purity of the sample and instrumental parameters, especially the temperature scan rate. A person skilled in the art can use routine optimization/calibration to set up instrumental parameters for a differential scanning calorimeter so that data comparable to the data presented here can be collected.

Abbreviations

The following abbreviations have been used.
Aq: aqueous
MeCN: acetonitrile
MeOH: methanol
DIPEA: diisopropylethylamine
DMF: dimethylformamide

Example 1

Preparation of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide (form C)

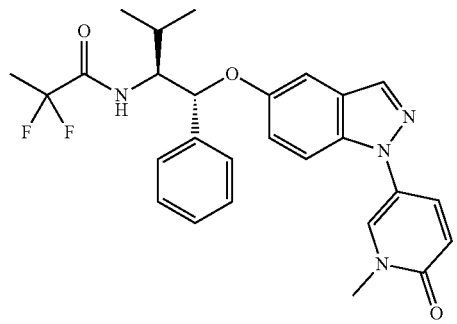 [SMILES: CC(C)[C@H](NC(=O)C(C)(F)F)[C@H](Oc1ccc2c(cnn2-c2ccc(=O)n(C)c2)c1)c1ccccc1]

Step A. Preparation of 5-[5-[(tert-butyldimethylsilyl)oxy]-1H-indazol-1-yl]-1-methyl-1,2-dihydropyridin-2-one

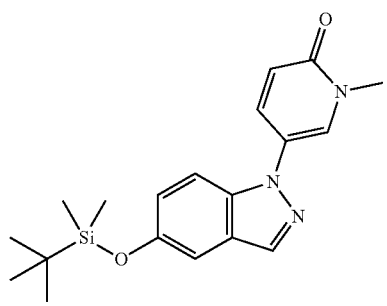 [SMILES: Cn1cc(-n2ncc3cc(O[Si](C)(C)C(C)(C)C)ccc32)ccc1=O]

Into a 2 L 4-necked, round-bottom flask, purged and maintained with an inert atmosphere of $N_2$, was placed a solution of 5-[(tert-butyldimethylsilyl)oxy]-1H-indazole (805 g, 3.2 mol) in toluene (8 L), 5-iodo-1-methyl-1,2-dihydropyridin-2-one (800 g, 3.4 mol) and $K_3PO_4$ (1.2 kg, 5.8 mol). Cyclohexane-1,2-diamine (63 g, 0.5 mol) was added followed by the addition of CuI (1.3 g, 6.8 mmol) in several batches. The resulting solution was stirred overnight at 102° C. The resulting mixture was concentrated under vacuum to yield 3.0 kg of the title compound as a crude black solid. LC/MS: m/z 356 [M+H]+.

Step B. Preparation of 5-(5-hydroxy-1H-indazol-1-yl)-1-methylpyridin-2(1H)-one

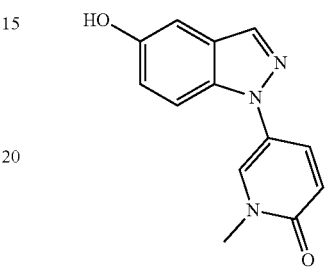

Into a 2 L 4-necked, round-bottom flask was placed 5-[5-[(tert-butyldimethylsilyl)oxy]-1H-indazol-1-yl]-1-methyl-1,2-dihydropyridin-2-one (3.0 kg, crude) and a solution of HCl (2 L, 24 mol, 36%) in water (2 L) and MeOH (5 L). The resulting solution was stirred for 1 hr at 40° C. and then evaporated to dryness. The resulting solid was washed with water (4×5 L) and ethyl acetate (2×0.5 L) to afford 480 g (61%, two steps) of the title product as a brown solid. LC/MS: m/z 242 [M+H]+. $^1$HNMR (300 MHz, DMSO-d6): δ 3.52 (3H, s), 6.61 (1H, m), 7.06 (2H, m), 7.54 (1H, m), 7.77 (1H, m), 8.19 (2H, m) 9.35 (1H, s).

Step C. Preparation of tert-butyl((1R,2S)-1-hydroxy-3-methyl-1-phenylbutan-2-yl)carbamate

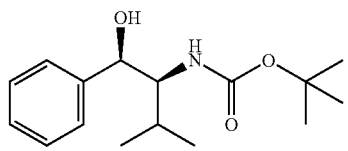 [SMILES: CC(C)[C@H](NC(=O)OC(C)(C)C)[C@H](O)c1ccccc1]

(S)-tert-butyl 3-methyl-1-oxo-1-phenylbutan-2-ylcarbamate (1.0 kg, 3.5 mol) was dissolved in toluene (4 L). Afterward, 2-propanol (2 L) was added, followed by triisopropoxyaluminum (0.145 L, 0.73 mol). The reaction mixture was heated at 54-58° C. for 1 hr under reduced pressure (300-350 mbar) to start azeotropic distillation. After the collection of 0.75 L condensate, 2-propanol (2 L) was added, and the reaction mixture was stirred overnight at reduced pressure to afford 4 L condensate in total. Toluene (3 L) was added at 20° C., followed by 2M HCl (2 L) over 15 min to keep the temperature below 28° C. The layers were separated (pH of aqueous phase 0-1) and the organic layer was washed successively with water (3 L), 4% $NaHCO_3$ (2 L) and water (250 mL). The volume of the organic layer was reduced from 6 L at 50° C. and 70 mbar to 2.5 L. The resulting mixture was heated to 50° C. and heptane (6.5 L) was added at 47-53° C. to maintain the material in solution. The temperature of the mixture was slowly decreased to 20°

C., seeded with the crystals of the title compound at 37° C. (seed crystals were prepared in an earlier batch made by the same method and then evaporating the reaction mixture to dryness, slurring the residue in heptane, and isolating the crystals by filtration), and allowed to stand overnight. The product was filtered off, washed with heptane (2×1 L) and dried under vacuum to afford 806 g (81%) of the title compound as a white solid. ¹HNMR (500 MHz, DMSO-d6): δ 0.81 (dd, 6H), 1.16 (s, 8H), 2.19 (m, 1H), 3.51 (m, 1H), 4.32 (d, 1H), 5.26 (s, 1H), 6.30 (d, 1H), 7.13-7.2 (m, 1H), 7.24 (t, 2H), 7.3-7.36 (m, 3H).

Step D. Preparation of (1R,2S)-2-amino-3-methyl-1-phenylbutan-1-ol hydrochloride Salt

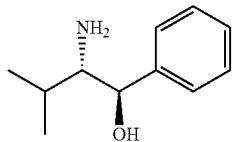

To a solution of HCl in propan-2-ol (5-6 N, 3.1 L, 16 mol) at 20° C. was added tert-butyl((1R,2S)-1-hydroxy-3-methyl-1-phenylbutan-2-yl)carbamate (605 g, 2.2 mol) in portions over 70 min followed by the addition of MTBE (2 L) over 30 min. The reaction mixture was cooled to 5° C. and stirred for 18 hr. The product was isolated by filtration and dried to afford 286 g of the title compound as an HCl salt (61% yield). The mother liquor was concentrated to 300 mL. MTBE (300 mL) was then added, and the resulting precipitation was isolated by filtration to afford additional 84 g of the title compound as a HCl salt (18% yield). Total 370 g (79%). ¹HNMR (400 MHz, DMSO-d6): δ 0.91 (dd, 6H), 1.61-1.81 (m, 1H), 3.11 (s, 1H), 4.99 (s, 1H), 6.08 (d, 1H), 7.30 (t, 1H), 7.40 (dt, 4H), 7.97 (s, 2H).

Step E. Preparation of (2S,3S)-2-isopropyl-1-(4-nitrophenylsulfonyl)-3-phenylaziridine

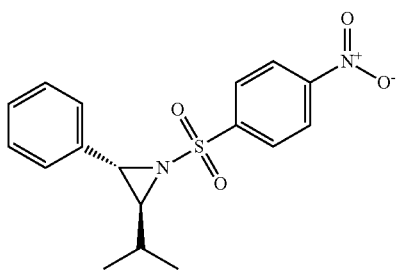 [SMILES: CC(C)[C@H]1[C@H](c2ccccc2)N1S(=O)(=O)c1ccc([N+](=O)[O-])cc1]

(1R,2S)-2-Amino-3-methyl-1-phenylbutan-1-ol hydrochloride (430 g, 2.0 mol) was mixed with DCM (5 L) at 20° C. 4-Nitrobenzenesulfonyl chloride (460 g, 2.0 mol) was then added over 5 min. Afterward, the mixture was cooled to −27° C. Triethylamine (1.0 kg, 10 mol) was slowly added while maintaining the temperature at −18° C. The reaction mixture was cooled to −30° C., and methanesulfonyl chloride (460 g, 4.0 mol) was added slowly while maintaining the temperature at −25° C. The reaction mixture was then stirred at 0° C. for 16 hr before adding triethylamine (40 mL, 0.3 mol; 20 mL, 0.14 mol and 10 mL, 0.074 mol) w at 0° C. in portions over 4 hr. Water (5 L) was subsequently added at 20° C., and the resulting layers were separated. The organic layer was washed with water (5 L) and the volume reduced to 1 L under vacuum. MTBE (1.5 L) was added, and the mixture was stirred on a rotavap at 20° C. over night and filtered to afford 500 g (70%) of the title product as a solid. ¹HNMR (400 MHz, CDCl₃): δ 1.12 (d, 3H), 1.25 (d, 3H), 2.23 (ddt, 1H), 2.89 (dd, 1H), 3.84 (d, 1H), 7.08-7.2 (m, 1H), 7.22-7.35 (m, 4H), 8.01-8.13 (m, 2H), 8.22-8.35 (m, 2H).

Step F. Preparation of N-((1R,2S)-3-methyl-1-(1-(1-methyl-6-oxo-1,6-dihydropyridin-3-yl)-1H-indazol-5-yloxy)-1-phenylbutan-2-yl)-4-nitrobenzenesulfonamide

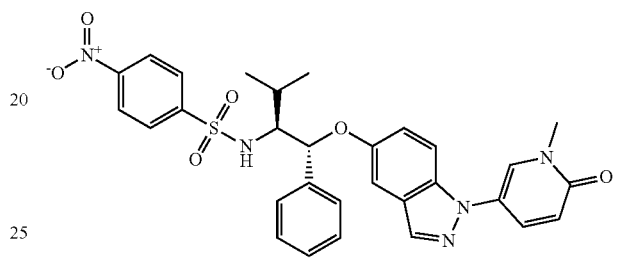

(2S,3S)-2-Isopropyl-1-(4-nitrophenylsulfonyl)-3-phenylaziridine (490 g, 1.3 mol) was mixed with 5-(5-hydroxy-1H-indazol-1-yl)-1-methylpyridin-2(1H)-one (360 g, 1.4 mol) in acetonitrile (5 L) at 20° C. Cesium carbonate (850 g, 2.6 mol) was added in portions over 5 min. The reaction mixture was then stirred at 50° C. overnight. Water (5 L) was added at 20° C., and the resulting mixture was extracted with 2-methyltetrahydrofuran (5 L and 2.5 L). The combined organic layer was washed successively with 0.5 M HCl (5 L), water (3×5 L) and brine (5 L). The remaining organic layer was concentrated to a thick oil, and then MTBE (2 L) was added. The resulting precipitate was filtered to afford 780 g (purity 71% w/w) of the crude title product as a yellow solid, which was used in the next step without further purification. ¹HNMR (400 MHz, DMSO-d6): δ 0.93 (dd, 6H), 2.01-2.19 (m, 1H), 3.50 (s, 3H), 3.74 (s, 1H), 5.00 (d, 1H), 6.54 (d, 1H), 6.78 (d, 1H), 6.95-7.15 (m, 4H), 7.23 (d, 2H), 7.49 (d, 1H), 7.69 (dd, 1H), 7.74 (d, 2H), 8.00 (s, 1H), 8.08 (d, 2H), 8.13 (d, 2H).

Step G. Preparation of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide

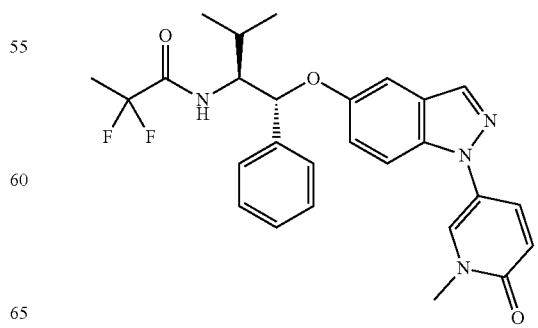

N-((1R,2S)-3-Methyl-1-(1-(1-methyl-6-oxo-1,6-dihydropyridin-3-yl)-1H-indazol-5-yloxy)-1-phenylbutan-2-yl)-4-nitrobenzenesulfonamide (780 g, 71% w/w) was mixed with DMF (4 L). DBU (860 g, 5.6 mol) was then added at 20° C. over 10 min. 2-Mercaptoacetic acid (170 g, 1.9 mol) was added slowly over 30 min, keeping the temperature at 20° C. After stirring for 1 hr, during which time the corresponding amine, 5-(5-((1R,2S)-2-amino-3-methyl-1-phenylbutoxy)-1H-indazol-1-yl)-1-methylpyridin-2(1H)-one, was produced, ethyl 2,2-difluoropropanoate (635 g, 4.60 mol) was added over 10 min at 20° C. The reaction mixture was stirred for 18 hr. Subsequently, additional ethyl 2,2-difluoropropanoate (254 g, 1.8 mol) was added, and the reaction mixture was stirred for an additional 4 hr at 20° C. Water (5 L) was then slowly added over 40 min, maintaining the temperature at 20° C. The water layer was extracted with isopropyl acetate (4 L and 2×2 L). The combined organic layer was washed with 0.5M HCl (4 L) and brine (2 L). The organic layer was then combined with the organic layer from a parallel reaction starting from 96 g of N-((1R,2S)-3-methyl-1-((1-(1-methyl-6-oxo-1,6-dihydropyridin-3-yl)-1H-indazol-5-yl)oxy)-1-phenylbutan-2-yl)-4-nitrobenzenesulfonamide, and concentrated to approximate 1.5 L. The resulting brown solution was filtered. The filter was washed twice with isopropyl acetate (2×0.5 L). The filtrate was evaporated until a solid formed. The solid was then co evaporated with 99.5% ethanol (1 L), affording the title compound 493 g (77%, two steps) as an amorphous solid.

Step H. Preparation of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide (form A)

The amorphous solid from the previous step (464 g, 0.94 mol) was dissolved in ethanol/water 2:1 (3.7 L) at 50° C. The reaction mixture was then seeded with crystals of the title compound as form A (0.5 g) at 47° C., and a slight opaque mixture was formed. The mixture was held at that temperature for 1 hr. Afterward, the temperature was decreased to 20° C. over 7 hr, and kept at 20° C. for 40 hr. The solid was filtered off, washed with cold (5° C.) ethanol/water 1:2 (0.8 L), and dried in vacuum at 37° C. overnight to afford 356 g (0.70 mol, 74%, 99.9% ee) of the title compound as a monohydrate (form A). LC/MS: m/z 495 [M+H]$^+$. $^1$H NMR (600 MHz, DMSO-d6)δ 0.91 (dd, 6H), 1.38 (t, 3H), 2.42 (m, 1H), 3.50 (s, 3H), 4.21 (m, 1H), 5.29 (d, 1H), 6.53 (d, 1H), 7.09 (d, 1H), 7.13 (dd, 1H), 7.22 (t, 1H), 7.29 (t, 2H), 7.47 (d, 2H), 7.56 (d, 1H), 7.70 (dd, 1H), 8.13 (d, 1H), 8.16 (d, 1H), 8.27 (d, 1H).

The seed crystals used in the step above were prepared from amorphous compound according to the following procedure:

A mixture of 5-(5-((1R,2S)-2-amino-3-methyl-1-phenylbutoxy)-1H-indazol-1-yl)-1-methylpyridin-2(1H)-one (1.0 mol eq), 2,2-difluoropropanoic (1.2 mol eq), HATU (1.5 mol eq) and DIPEA (3.0 mol eq) in DMF (8 volumes) was stirred at room temperature for several hours. Afterward, the reaction mixture was poured into water and extracted with DCM (3×20 volumes), dried over $Na_2SO_4$ and concentrated. The residue was purified by preparative HPLC. This product (401 mg) was weighed into a glass vial. Ethanol (0.4 mL) was added, and the vial was shaken and heated to 40° C. to afford a clear, slightly yellow solution. Ethanol/Water (0.4 mL, 50/50% vol/vol) was added. Crystallization started to occur within 5 min, and, after 10 min, a white thick suspension formed. The crystals were collected by filtration to afford the title compound as a monohydrate (form A).

Step I. Preparation of 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide (Form C)

2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide as monohydrate—form A (100 g) was dissolved in isopropanol (1.2 L) at 50-55° C. and the resulting solution was filtered. This was then distilled at ≤50° C. under reduced pressure to about 0.3 L and the water content of the solution checked (target <0.20% w/w). If the target water content was not achieved, the solution was further dried by repeated addition of isopropanol (1.2 L) and distillation back to about 0.3 L until the target was met. Further isopropanol (0.3 L) was added, the mixture heated to 73-77° C. and refluxed for 0.5-2 hr. The resulting solution was then distilled at 45-80° C. under reduced pressure to about 0.3 L, refluxed for 0.5-1 hr and then cooled to 58-62° C. over about 1 hr. Seed crystals of the title compound (0.1 g) were added and the mixture was cooled to 22-26° C. over 3.5-4 hr. The mixture was stirred at 22-26° C. for 3-5 hr and then n-heptane (0.6 L) was added over 10-12 hr. This was then heated to 48-52° C. over about 1 hr, cooled to 22-26° C. over about 1 hr, heated again to 48-52° C. over about 1 hr and finally cooled to 2-7° C. over 5-6 hr. The mixture was stirred for 6-10 hr, filtered and the resulting solid was washed with n-heptane (about 0.1 L). The solid was dried under vacuum at 50-55° C. to give the title compound (form C) (80-90 g, 80-90% yield).

The seed crystals used in the previous step were prepared using the following procedure: 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide (as a monohydrate) (15 g) was dissolved in isopropanol (180 ml) at about 50° C. The resulting solution was then distilled to ~45 ml and stirred, during which solid was observed to crystallise out. The mixture was cooled to about 25° C. over about 30 min, stirred for about 5 hr and then heated to about 35° C. To this was added n-heptane (12 ml) over about 4 hr and the mixture was stirred for about 4 hr. The resulting solid was collected by filtration and dried under vacuum at about 50° C. to give the title compound (form C).

Biological Activity
GRE Agonist Assay

A reporter cell line (ChagoK1 18:7:2 s4/GRE) was established by stable transfection of the human bronchogenic carcinoma cell line, ChaGo K1 (ATCC: HTB 168) with a MMTV-GRE-LacZ reporter construct. The generated cell line allows for identification of compounds showing agonist activity at the human glucocorticoid receptor (GR) via induction of LacZ gene expression. Ligand-activated GR binds to the Glucocorticoid Response Element (GRE) in the promoter of the LacZ gene and transcription is initiated. The resulting beta-galactosidase activity is measured through a colour reaction (change in absorbance).

Cryo-preserved ChagoK1 18:7:2 s4/GRE cells were suspended in RPMI medium with 10% FBS, 1% NEAA and 1% sodium pyruvate, and seeded as 50000 cells/200 ul/well in 96-well plates and cultured at 37° C. with 5% $CO_2$ and 95% humidity for 24 hours. 1 μl compound was added at different concentrations to the cells and incubated for another 24 hours. Cells were washed once in PBS and lysed with 50 al of 0.1% Triton-X for 10 min at room temperature. 40 μl of reaction mixture (2.5 mM MgCl$_2$, 0.1 M β-mercaptoethanol, 1.7 mg/ml ONPG and 42.5 mM sodium phosphate, pH 7.5), was added to each well and kept at 37° C. for 60 min. The reaction was then terminated by addition of 100 al stop solution (300 mM glycine, 15 mM EDTA, pH 11.3, adjusted with NaOH). The plates were measured at 420 nm for absorbance in a SpectraMax reader (Molecular Device).

The relative efficacy (% effect) of a compound is calculated based on the full agonist effect of dexamethasone:

% Effect=((Sample abs−min abs)/(max abs−min abs))×100

To calculate EC50, max, min and slope factor for each compound, a concentration response curve is fitted by plotting % Effect versus compound concentration using the 4 parameter logistic equation:

$y=A+(B-A)/(1+((10C)/x)D)$

Where A=min Y, B=max Y, C=log EC50 and D=Slope factor

GRE Antagonist Assay

A reporter cell line (ChagoK1 18:7:2 s4/GRE) was established by stable transfection of the human bronchogenic carcinoma celline, ChaGo K1 (ATCC: HTB 168) with a MMTV-GRE-LacZ reporter construct. The generated cell line allows for identification of compounds showing antagonist activity at the human glucocorticoid receptor (GR) via reduction of LacZ gene expression. Dexamethasone-activated GR binds to the Glucocorticoid Response Element (GRE) in the promoter of the LacZ gene and transcription is initiated. Antagonistic properties of compounds are assessed as beta-galactosidase intensity reduction from pre-stimulation with dexamethasone through a colour reaction (change in absorbance).

Cryo-preserved ChagoK1 18:7:2 s4/GRE cells were suspended in RPMI medium with 10% FBS, 1% NEAA and 1% sodium pyruvate, and seeded as 50000 cells/200 ul/well in 96-well plates and cultured at 37° C. with 5% CO$_2$ and 95% humidity for 24 hr. Cells were pre-stimulated with 2 µl dexamethasone (70 nM final conc) for 4-5 hr, before addition of 1 µl compound at different concentrations and incubation for an additional 24 hr. Cells were washed once in PBS and lysed with 50 µl of 0.1% Triton-X for 10 min at room temperature. 40 µl of reaction mixture (2.5 mM MgCl$_2$, 0.1 M β-mercapto ethanol, 1.7 mg/ml ONPG and 42.5 mM sodium phosphate, pH 7.5), was added to each well and kept at 37° C. for 60 min. The reaction was then terminated by addition of 100 µl stop solution (300 mM glycine, 15 mM EDTA, pH 11.3, adjusted with NaOH). The plates were measured at 420 nm for absorbance in a SpectraMax reader (Molecular Device).

The relative efficacy (% effect) of a compound is calculated based on the full antagonist effect of the reference compound Mifepristone (RU486):

% Effect=((Sample abs−min abs)/(max abs−min abs))×100

To calculate IC50, max, min and slope factor for each compound, a concentration response curve is fitted by plotting % Effect versus compound concentration using the 4 parameter logistic equation:

$y=A+(B-A)/(1+((10C)/x)D)$

Where A=min Y, B=max Y, C=log IC50 and D=Slope factor

Table 2 shows the results of these assays with the compound of Example 1. "TA" is the transactivation measured in agonist mode in the GRE Agonist Assay, and in antagonist mode in the GRE Antagonist Assay

TABLE 2

Results from Biological Assays

| Example | TA agonist pEC50 | TA agonist Observed max Effect at 1 µM (%) | TA antagonist pIC50 | TA antagonist Observed max Effect at 1 µM (%) |
|---|---|---|---|---|
| 1 | 7.9 | 39 | 6.8 | 70 |

In Vitro Human Whole Blood

The anti-inflammatory activity of compounds and prednisolone was determined in vitro by their ability to inhibit the release of TNFα from whole blood stimulated with LPS. Venous blood from human donors was collected and anticoagulated with sodium heparin and transferred to a sterile polystyrene round bottomed plate (Corning) at 190 µL per well.

Compounds were prepared from 10 mM stock solutions in dimethylsulfoxide (DMSO, Sigma) by serially diluting 1/3 in DMSO to produce a master plate with the top concentration at 3.33 mM and the lowest concentration at 0.1 µM. Compounds from the master plate were added to the blood at 1 µL/well (1/200) dilution to give final concentrations ranging between 16 0.7 µM and 0.5 nM. Control wells received 1 µL DMSO only and the final DMSO concentration in all wells was 0.5%. The samples were gently mixed and placed into a humidified incubator (95% air/5% CO$_2$) at 37° C. and incubated for 45 min.

LPS (*E. coli* serotype 0127:B8, Sigma) was diluted in PBS without CaCl$_2$/MgCl$_2$ (Gibco) to afford a working solution at 600 µg/mL. 10 µL was added to each well to give a final LPS concentration of 30 µg/mL. Unstimulated controls received PBS only at 10 µL/well. The samples were, again, gently mixed, and the plates incubated overnight for 18 hr. Following incubation, the blood was centrifuged at 700×g for 5 min, and the plasma removed and transferred to freeze at −20° C. before assay for TNFα release.

TNFα protein levels were determined using an AlphaLISA hTNFα kit (Perkin Elmer) according to the manufacturer's instructions. Briefly, the samples were allowed to return to room temperature and centrifuged at 1500×g for 5 min. Samples were diluted 1/5 (5 µL sample in 20 µL AlphaLISA buffer). At the same time, a standard curve of TNFα was prepared by serial 1/3 dilutions from a stock solution (5000-2 µg/mL). 5 µL sample/standard curve were transferred to a 384-well Optiplate™, and to this was added 20 µL anti-humanTNFα acceptor beads/biotinylated antibody mix. The plate was incubated at room temperature for 60 min. After this incubation, 25 µL streptavidin donor beads were added, and the plate was incubated for a further 60 min in the dark at room temperature. The samples were read at 615 nm with excitation at 680 nm using an Envision plate reader. TNFα in the samples was determined by extrapolation from the standard curve and expressed as pg/mL.

The % inhibition of TNFα was determined by the equation:

% inhibition=(1−(A−B)/(C−B))×100

Here, A=TNFα in LPS stimulated samples containing compound, B=TNFα in unstimulated samples. and C=TNFα in LPS stimulated samples without compound. Percent inhibition was plotted against concentration, and a curve graphed using a 4-parameter curve fit (Xlfit 4.1) to determine the $pIC_{50}$.

TABLE 3

TNFα $pIC_{50}$ for Prednisolone and the Compounds of Example 1

| Compound | $pIC_{50}$ |
|---|---|
| Prednisolone | 6.5 (n = 31) |
| Example 1 | 6.2 (n = 16) |

Tyrosine Aminotransferase ("TAT") mRNA Expression In Vitro Assay

The impact of test compounds on hyperglycemic events were assessed by looking at changes in mRNA expression of the gene encoding tyrosine aminotransferase (TAT), which is under direct regulation of the glucocorticoid receptor in human hepatocytes.

Experimental Outline

Human cryopreserved primary hepatocytes (BioreclamationIVT, M00995-P lot EPB) were plated to 24-well collagen I-coated plates (Becton Dickinson, 354408). Cells were allowed to attach for 4 hr before being challenged with test compounds overnight (18 hr). Cells were harvested and total RNA isolated using RNeasy Plus Mini Kit (Qiagen, 74136) followed by cDNA synthesis using High Capacity cDNA reverse transcription kit (Applied Biosystems, 4368813). Real-time RT PCR was performed on an Applied Biosystems 7500 PCR cycler, using Taqman primers for TAT (Life technologies, Hs00356930_m1) and the reference gene hypoxanthine phosphoribosyltransferase 1 (Life technologies, Hs99999909_m1).

Protocol

Human cryopreserved primary hepatocytes were transferred in to pre-warmed (37° C.) plating medium (BioreclamationIVT, Z990003) and diluted to $0.7 \times 10^6$ viable cells/mL. 500 μL of the cell suspension was plated to each well of a collagen I coated 24-well plate and cells were allowed to sediment and attach at 37° C. for 4 hr. After incubation, the media was gently discarded and exchanged for insulin, glucose, glutamine, pyruvate free media (BioreclamationIVT, S00304), containing compounds of interest, prednisolone at 1 μM, dissolved in DMSO (final DMSO concentration 0.01%), or DMSO alone as control. The plates were then incubated at 37° C. for an additional 18 hr. Media was discarded, and total RNA isolation (Qiagen) and cDNA synthesis (Applied Biosystems) performed according to the manufactures protocol. Real-time RT PCR was carried out using TaqMan reagents (Life technologies) on the 7500 PCR cycler, and Ct-values for TAT gene expression was normalised to the control gene and expressed as fold change compared to DMSO control using the $2^{-\Delta\Delta Ct}$ method.

TABLE 4

Fold Change Tyrosine Aminotransferase Gene Expression Relative to Control

| Compound | Fold Change Relative to Control (1 μM) |
|---|---|
| Prednisolone | 2.5 (1.4-4.2, n = 8) |
| Example 1 | 1.0 (0.8-1.4, n = 6 |

The invention claimed is:

1. A crystalline form 2,2-difluoro-N-[(1R,2S)-3-methyl-1-{[1-(1-methyl-6-oxo-1,6-dihydropyridin-3-yl)-1H-indazol-5-yl]oxy}-1-phenylbutan-2-yl]propanamide:

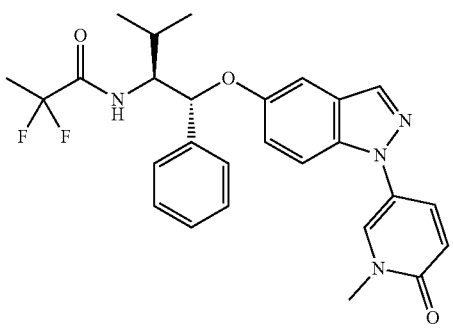 [SMILES: CC(C)[C@H](NC(=O)C(C)(F)F)[C@H](Oc1ccc2c(cnn2-c2ccc(=O)n(C)c2)c1)c1ccccc1]

that has an X-ray powder diffraction pattern with at least one specific peak at 2θ about=7.3, 8.7, 12.5, and/or 15.3° when measured using CuKα radiation.

2. A compound according to claim 1, characterised in that it has an X-ray powder diffraction pattern with at least 3 specific peaks at 2θ about=7.3, 8.7, 12.5, 15.3 and/or 19.0° when measured using CuKα radiation.

3. A compound according to claim 1, characterised in that it has an X-ray powder diffraction pattern with specific peaks at 2θ about=7.3, 8.7, 12.5, 19.4 and 23.6° when measured using CuKα radiation.

4. A compound according to claim 1, characterised in that it has an X-ray powder diffraction pattern with specific peaks at 2θ about=7.3, 8.7, 11.4, 12.5, 14.5, 15.3, 17.6, 19.4, 23.6 and 25.7° when measured using CuKα radiation.

5. A compound according to claim 1, characterised in that it has an X-ray powder diffraction pattern substantially as shown in FIG. 1, when measured using CuKα radiation.

6. A pharmaceutical composition comprising a compound as claimed in claim 1 in association with a pharmaceutically acceptable adjuvant, diluent or carrier.

7. The compound according to claim 1 for use as a medicament.

8. The compound according to claim 1 for use in treating asthma.

9. The compound according to claim 1 for use in treating rheumatoid arthritis.

10. A method of treating asthma, which comprises administering to the patient a therapeutically effective amount of a compound as claimed in claim 1.

11. A method of treating rheumatoid arthritis, which comprises administering to the patient a therapeutically effective amount of a compound as claimed in claim 1.

* * * * *